US012804285B2

(12) United States Patent
Hosogai et al.

(10) Patent No.: US 12,804,285 B2
(45) Date of Patent: Nov. 17, 2026

(54) IMAGING DEVICE AND ENDOSCOPE

(71) Applicant: OLYMPUS MEDICAL SYSTEMS CORP., Hachioji (JP)

(72) Inventors: Katsumi Hosogai, Tsukuba (JP); Masashi Saito, Akishima (JP); Hideki Kato, Hino (JP)

(73) Assignee: OLYMPUS MEDICAL SYSTEMS CORP., Hachioji (JP)

( * ) Notice: Subject to any disclaimer, the term of this patent is extended or adjusted under 35 U.S.C. 154(b) by 183 days.

(21) Appl. No.: 18/753,806

(22) Filed: Jun. 25, 2024

(65) Prior Publication Data

US 2025/0000350 A1 Jan. 2, 2025

Related U.S. Application Data

(60) Provisional application No. 63/523,472, filed on Jun. 27, 2023.

(51) Int. Cl.

| | |
|---|---|
| ***H04N 25/77*** | (2023.01) |
| ***A61B 1/00*** | (2006.01) |
| ***A61B 1/04*** | (2006.01) |
| ***H04N 25/44*** | (2023.01) |
| ***H04N 25/445*** | (2023.01) |
| ***H04N 25/778*** | (2023.01) |
| ***H10F 39/00*** | (2025.01) |

(52) U.S. Cl.
CPC ......... *H04N 25/77* (2023.01); *A61B 1/00013* (2013.01); *A61B 1/042* (2013.01); *H04N 25/44* (2023.01); *H04N 25/445* (2023.01); *H04N 25/778* (2023.01); *H10F 39/018* (2025.01)

(58) Field of Classification Search
CPC ...... H04N 25/44; H04N 25/445; H04N 25/77; H04N 25/778; A61B 1/00013; A61B 1/042; A61B 1/051; H10F 39/018
See application file for complete search history.

(56) References Cited

U.S. PATENT DOCUMENTS 11,588,988 B2 * 2/2023 Jang ........................ H04N 25/78
12,532,092 B2 * 1/2026 Han ........................ H04N 25/77
(Continued)

FOREIGN PATENT DOCUMENTS

JP 2009-49740 A 3/2009

*Primary Examiner* — Lin Ye
*Assistant Examiner* — Chriss S Yoder, III
(74) *Attorney, Agent, or Firm* — WHDA, LLP

(57) ABSTRACT

The imaging device of the present invention is an imaging device including a pixel array in which pixels including photoelectric conversion elements that perform photoelectric conversion are disposed in a matrix, wherein the photoelectric conversion elements of a plurality of pixels adjacent in a column direction share a floating diffusion that accumulates photoelectrically converted charge, vertical signal lines that output signals based on the charge accumulated in the floating diffusion to the outside are wired to each column of the pixel array, a column selection signal line that transmits a selection control signal selecting one of a plurality of vertical signal lines adjacent in a row direction is wired within a region of the pixel array, and one column processing circuit that processes the signal is provided for the plurality of vertical signal lines selected by the selection control signal.

13 Claims, 6 Drawing Sheets

(56) References Cited

U.S. PATENT DOCUMENTS

2010/0259662 A1* 10/2010 Oike .................... H04N 25/00
348/308
2012/0188424 A1* 7/2012 Li ......................... H10F 39/803
348/294
2021/0400224 A1* 12/2021 Gocho ................... H04N 25/78
2023/0283918 A1* 9/2023 Zhou ................... H10F 39/8053
348/301

* cited by examiner

IMAGING DEVICE AND ENDOSCOPE

BACKGROUND OF THE INVENTION

Field of the Invention

The present invention relates to an imaging device and an endoscope.

Description of Related Art

In the related art, charge-coupled device (CCD) sensors, complementary metal-oxide-semiconductor (CMOS) sensors, and the like are used as imaging elements. In recent years, imaging elements have been developed to have more pixels and smaller sizes, and pixel pitches, which are distances from centers to centers between adjacent pixels of imaging elements, have become shorter.

As imaging pixels become smaller, the effects of variations in the arrangement of circuits constituting the pixels become more noticeable, and thus a layout that maintains symmetry of the pixels is required. For that reason, it is desirable to be able to dispose pixels with a high degree of freedom.

In the imaging device described in Patent Document 1, a plurality of pixels share part of circuits constituting the pixels, thereby making it easier to lay out peripheral circuits such as an analog-to-digital converter (ADC).

PATENT DOCUMENTS

[Patent Document 1] Japanese Unexamined Patent Application, First Publication No. 2009-049740

SUMMARY OF THE INVENTION

However, as imaging elements become smaller, there is a demand to be able to dispose pixels with a higher degree of freedom.

In light of the above, an object of the present invention is to provide an imaging device in which it is possible to dispose pixels with a higher degree of freedom, and an endoscope including the imaging device.

In order to solve the above problems, the present invention proposes the following means.

An imaging device according to a first aspect of the present invention is an imaging device including a pixel array in which pixels including photoelectric conversion elements that perform photoelectric conversion are disposed in a matrix, wherein the photoelectric conversion elements of a plurality of pixels adjacent in a column direction share a floating diffusion that accumulates photoelectrically converted charge, vertical signal lines that output signals based on the charge accumulated in the floating diffusion to the outside are wired to each column of the pixel array, a column selection signal line that transmits a selection control signal selecting one of a plurality of vertical signal lines adjacent in a row direction is wired within a region of the pixel array, and one column processing circuit that processes the signal is provided for the plurality of vertical signal lines selected by the selection control signal.

In a transmitting and receiving system, the imaging device, and the endoscope according to the present invention, it is possible to dispose the pixels with a higher degree of freedom.

DETAILED DESCRIPTION OF THE INVENTION

One embodiment of the present invention will be described with reference to FIGS. 1 to 6. An example of an endoscope system including an imaging device will be described below.

Figure 1:
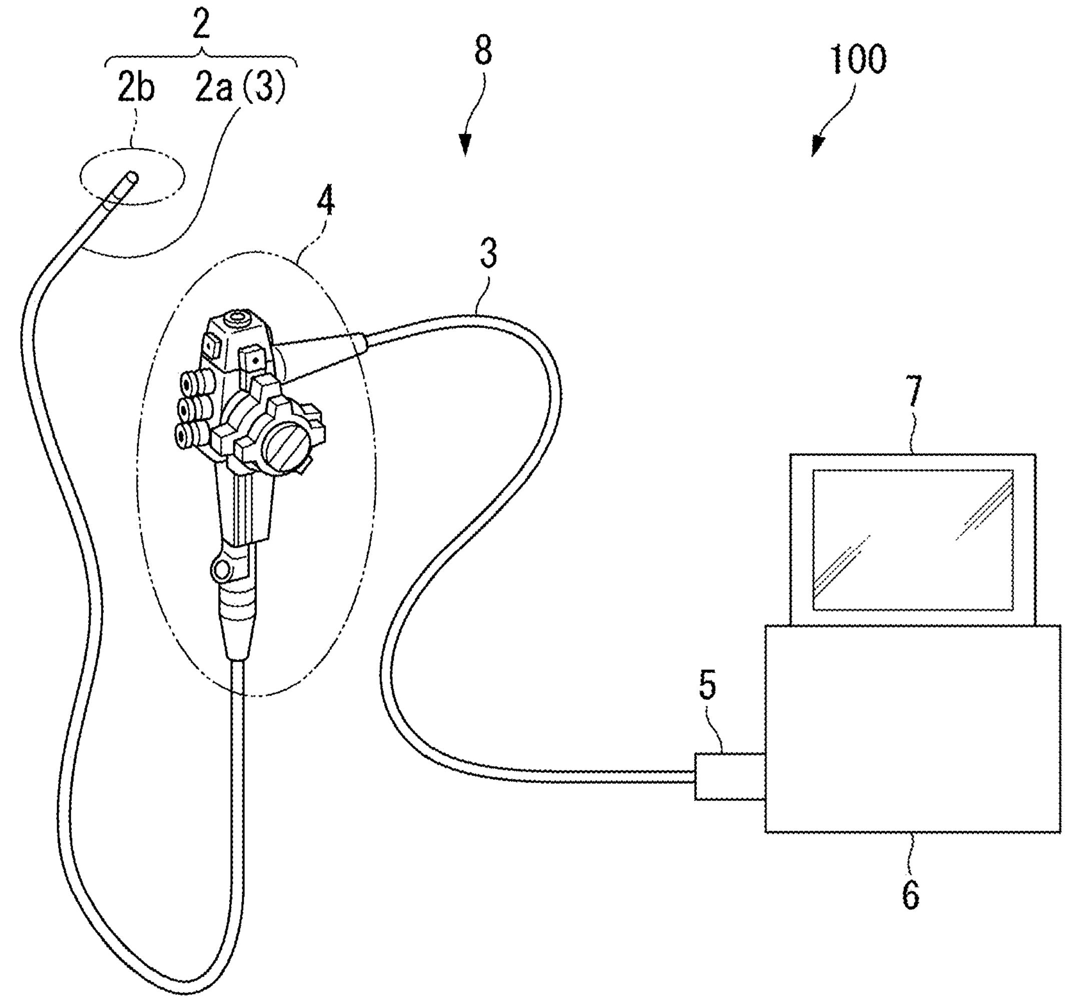
FIG. 1 is a configuration diagram of an endoscope system according to one embodiment.

FIG. 1 is a configuration diagram of an endoscope system 100 according to one embodiment of the present invention. The endoscope system 100 includes an endoscope insertion unit 2, a transmission cable 3, an operation unit 4, a connector unit 5, a control unit 6, and a display device 7. The endoscope insertion unit 2, the transmission cable 3, the operation unit 4, and the connector unit 5 form a scope 8 (endoscope).

Figure 2:
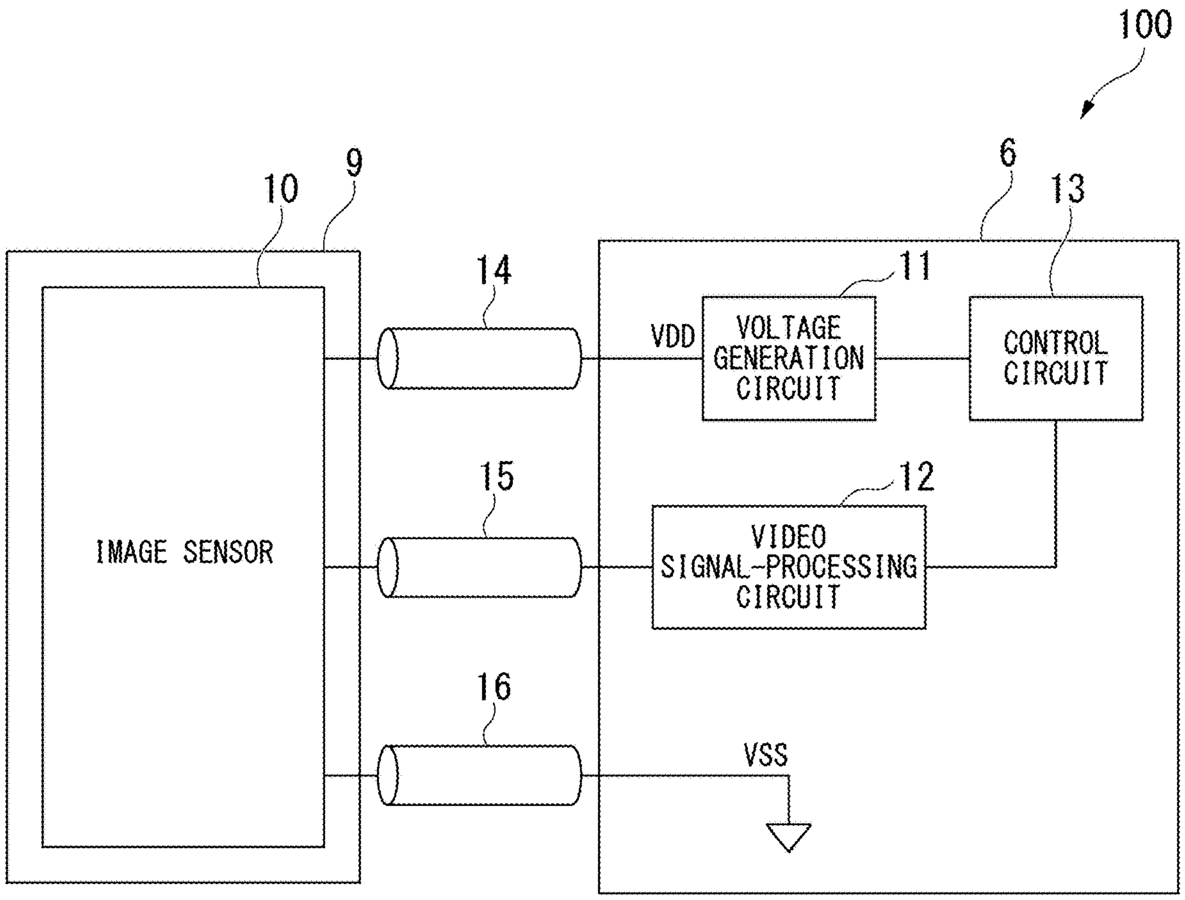
FIG. 2 is a diagram showing configurations of a camera unit and a control unit of the endoscope system.

The endoscope insertion unit 2 includes an insertion unit 2*a*. The insertion unit 2*a* is a part of the transmission cable 3. The insertion unit 2*a* is inserted into a living body that is a subject. The endoscope insertion unit 2 generates a video signal by capturing an image of the inside of the subject. The endoscope insertion unit 2 outputs the generated video signal to the control unit 6. A camera unit 9 shown in FIG. 2 is disposed at a tip 2*b* of the insertion unit 2*a*. The operation unit 4 is connected to an end portion of the insertion unit 2*a* on a side opposite to the tip 2*b*. The operation unit 4 receives various operations for the endoscope insertion unit 2 from a user.

The transmission cable 3 connects the camera unit 9 to the connector unit 5. A video signal generated by the camera unit 9 is output to the connector unit 5 via the transmission cable 3.

The connector unit 5 is connected to the transmission cable 3 and the control unit 6. The connector unit 5 performs predetermined processing on the video signal output from the endoscope insertion unit 2. The connector unit 5 outputs the video signal to the control unit 6.

The control unit 6 performs image processing on the video signal output from the connector unit 5. Further, the control unit 6 comprehensively controls the entire endoscope system 100.

The display device 7 displays an image on the basis of the video signal processed by the control unit 6. In addition, the display device 7 displays various types of information related to the endoscope system 100.

FIG. 2 is a diagram showing configurations of the camera unit 9 and the control unit 6. The endoscope system 100 includes the camera unit 9 and the control unit 6. The camera unit 9 is disposed at the tip 2*b* of the scope 8. The operation unit 4, the connector unit 5, and the display device 7 are not shown in FIG. 2. The transmission cable 3 shown in FIG. 1 includes a power supply line 14, a video signal line 15, and a reference line 16 shown in FIG. 2. The camera unit 9 and the control unit 6 are connected to each other by the power supply line 14, the video signal line 15, and the reference line 16.

The endoscope system 100 includes a light source device that generates illumination light with which the subject is irradiated. The light source device is not shown in FIG. 2.

The camera unit 9 includes an image sensor 10. The control unit 6 includes a voltage generation circuit 11, a video signal-processing circuit 12, and a control circuit 13.

For example, the voltage generation circuit 11 is a voltage regulator. The voltage generation circuit 11 generates a power supply voltage VDD, which is a DC voltage, and outputs the power supply voltage VDD to the power supply line 14. For example, the power supply voltage VDD is 3.3 V. The power supply line 14 is a signal line disposed in the transmission cable 3. The power supply line 14 transfers the power supply voltage to the camera unit 9. The power supply voltage transferred by the power supply line 14 is input to the image sensor 10 of the camera unit 9.

The reference line 16 is a signal line disposed in the transmission cable 3. The reference line 16 transfers a reference voltage VSS, which is lower than the power supply voltage VDD, from the control unit 6 to the camera unit 9. For example, the reference voltage VSS is a ground voltage (0 V). The reference voltage VSS transferred by the reference line 16 is input to the image sensor 10 of the camera unit 9.

The image sensor 10 generates a video signal on the basis of the power supply voltage VDD and the reference signal VSS and outputs the video signal to the video signal line 15. The video signal line 15 is a signal line disposed in the transmission cable 3. The video signal line 15 transfers the video signal to the control unit 6.

The video signal-processing circuit 12 receives the video signal transferred by the video signal line 15. The video signal-processing circuit 12 performs predetermined signal processing on the video signal and outputs the video signal to the display device 7. The control circuit 13 controls operations of the voltage generation circuit 11 and the video signal-processing circuit 12.

Figure 3:
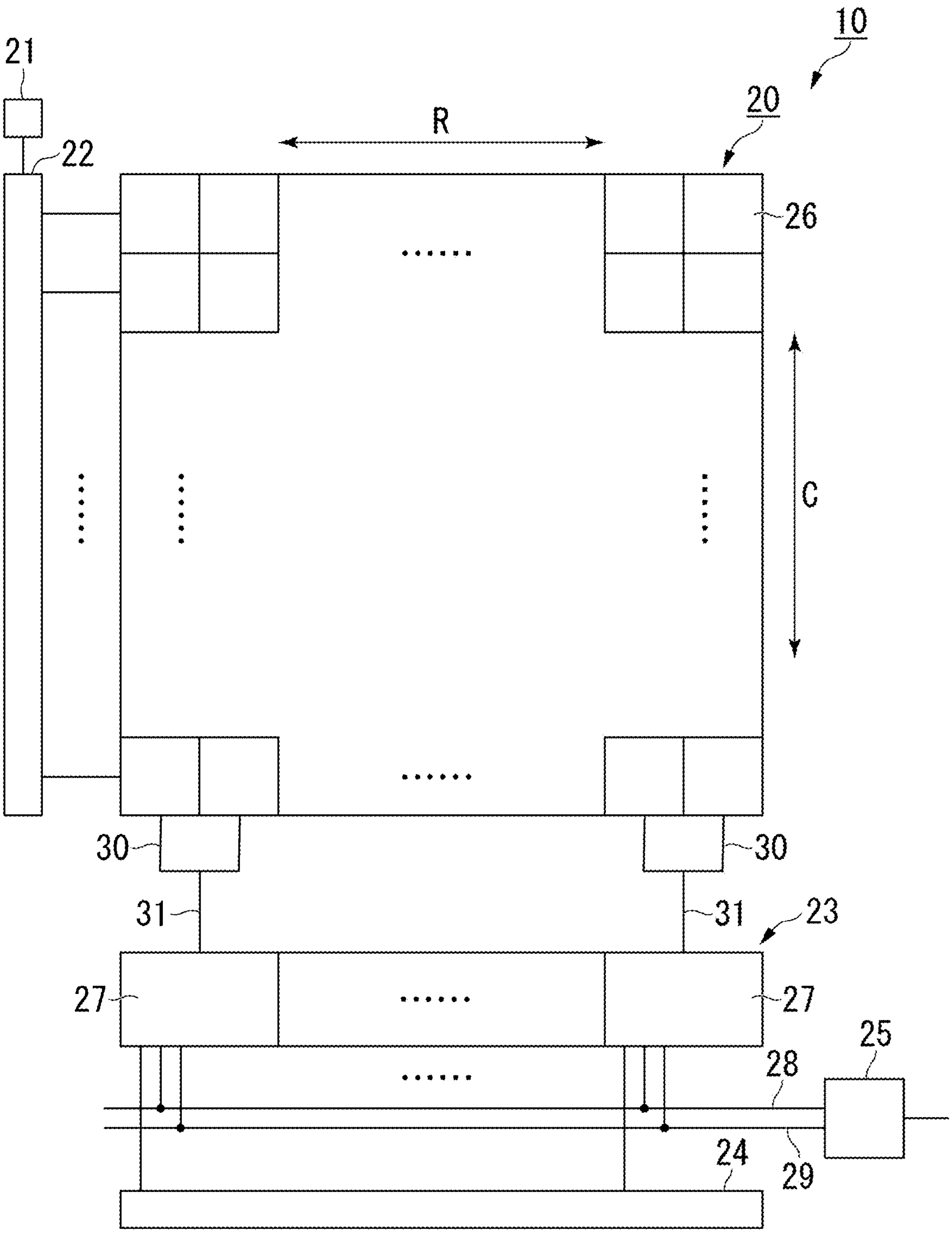
FIG. 3 is a configuration diagram of an image sensor of the endoscope system.

FIG. 3 is a configuration diagram of the image sensor 10. The image sensor (imaging element) 10 includes an imaging unit 20, a voltage generation circuit 21, a vertical selection circuit 22, a column circuit unit 23, a horizontal selection circuit 24, and an output unit 25. The circuitry in the image sensor 10 operates in response to a clock signal supplied from a clock generation circuit not shown in FIG. 3. The control unit 6 may include the clock generation circuit, and the clock signal generated by the clock generation circuit may be transferred to the camera unit 9.

The imaging unit 20 includes a plurality of pixels 26 disposed in a matrix. The plurality of pixels 26 disposed in a matrix are also called a "pixel array." The pixel array forms an arrangement of N rows and M columns. The number of rows (N) is 2 or more, and the number of columns (M) is 2 or more. The numbers of rows and columns do not need to be the same. Each of the pixels 26 outputs a first pixel signal having a reset level and a second pixel signal having a signal level.

In the pixel array, vertical signal lines 30 extending in a vertical direction, that is, in a column direction C, are wired for each column. The vertical signal lines 30 are connected to the plurality of pixels 26 disposed in the column direction C. The vertical signal lines 30 adjacent to each other in a row direction R are connected to one shared vertical signal line 31 outside the pixel array. In the present embodiment, two vertical signal lines 30 adjacent to each other in the row direction R are connected to one shared vertical signal line 31 outside the pixel array.

The voltage generation circuit 21 generates a drive voltage higher than the reference voltage VSS and lower than the power supply voltage VDD on the basis of the power supply voltage VDD and the reference voltage VSS. The drive voltage is output to each pixel 26 via the vertical selection circuit 22.

The vertical selection circuit 22 selects one row from among N rows in the pixel array. The vertical selection circuit 22 controls operations of the plurality of pixels 26 disposed in the selected row. The vertical selection circuit 22 outputs a control signal for controlling the plurality of pixels 26 for each row.

The column circuit unit 23 includes a plurality of column processing circuits 27. The column processing circuits 27 are disposed for each of a plurality of columns in the pixel array. In the present embodiment, one of the column processing circuits 27 is disposed for every two columns in the pixel array.

The column processing circuits 27 are connected to the shared vertical signal lines 31. The column processing circuits 27 are disposed outside a region of the pixel array parallel with pixel columns of the pixel array. The column processing circuits 27 are electrically connected to the plurality of pixels 26 via the vertical signal lines 30 and the shared vertical signal lines 31. The column processing circuits 27 hold the first pixel signals and the second pixel signals output from the pixels 26.

Each of the column processing circuits 27 is connected to a first horizontal signal line 28 and a second horizontal signal line 29 that extend in a horizontal direction, that is, in the row direction R. A selection pulse is output from the horizontal selection circuit 24 to each of the column processing circuits 27. The column processing circuit 27 selected on the basis of the selection pulse outputs the first pixel signals to the first horizontal signal line 28 and outputs the second pixel signals to the second horizontal signal line 29.

The first horizontal signal line 28 and the second horizontal signal line 29 are connected to the output unit 25. The horizontal selection circuit 24 sequentially outputs selection pulses to the column processing circuits 27 to sequentially select the column processing circuits 27. The first pixel signals and the second pixel signals output from the column processing circuits 27 selected by the horizontal selection circuit 24 are transferred to the output unit 25.

The output unit 25 generates a video signal on the basis of the first pixel signal and the second pixel signal. For example, the video signal is a difference between the first pixel signal and the second pixel signal. The output unit 25 outputs the video signal to the video signal line 15.

Figure 4:
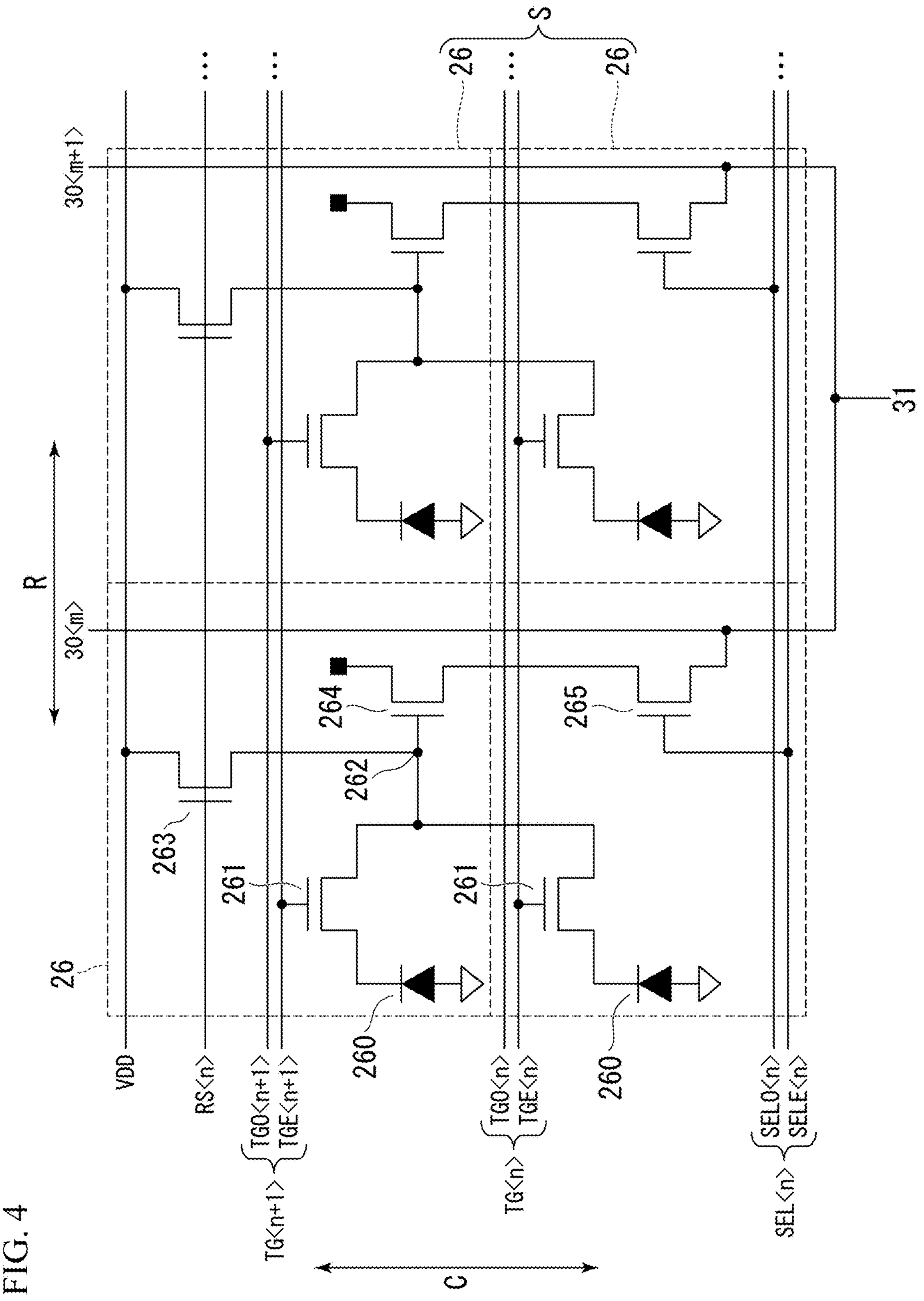
FIG. 4 is a circuit diagram of a part of a pixel array of the image sensor.

FIG. 4 is a circuit diagram of a part of the pixel array. The pixel 26 includes a photoelectric conversion element 260, a transfer transistor 261, a floating diffusion (FD) 262, a reset transistor 263, an amplification transistor 264, and a selection transistor 265.

The photoelectric conversion element 260 is a photodiode. The photoelectric conversion element 260 performs photoelectric conversion on light incident on the photoelectric conversion element 260 and generates a charge in accordance with an amount of the light. The transfer transistor 261 transfers the charge generated by the photoelectric conversion element 260 to the FD 262. The FD 262 holds the charge transferred by the transfer transistor 261.

The photoelectric conversion elements 260 of the plurality of pixels 26 adjacent in the column direction C share the FD 262 that accumulates the photoelectrically converted charge. In the present embodiment, the pixels 26 that share the FD 262 are two pixels 26 adjacent to each other in the column direction C. In the following description, the plurality of pixels 26 that share the FD 262 are also referred to as "shared pixels S."

The reset transistor 263 resets a voltage of the FD 262 to a voltage corresponding to the power supply voltage VDD. Thus, the reset transistor 263 resets the charge held in the FD 262. The amplification transistor 264 generates a pixel signal by amplifying a signal based on the voltage of the FD 262. The selection transistor 265 outputs the pixel signal to the vertical signal line 30. The first pixel signal having a reset level and the second pixel signal having a signal level are output from the pixel 26.

The vertical selection circuit 22 outputs a reset control signal RS, a transfer control signal TG, and a selection control signal SEL.

A reset signal line that transmits the reset control signal RS is wired for each of a plurality of rows in which the shared pixels S are disposed. In the present embodiment, the reset signal line is wired for every two rows. The reset signal line is wired to pass through a region of one of the pixels 26 in a region of the shared pixels S. The reset signal line is connected to the reset transistor 263. The reset signal line may also be wired in the middle of the shared pixels S.

A transfer control signal line that transmits the transfer control signal TG is wired for each row of the pixel array. The transfer control signal line is connected to the transfer transistor 261. The transfer control signal line includes a transfer control signal line that transmits an odd column transfer control signal TGO for controlling the transfer transistors 261 of the pixels 26 in odd columns, and a transfer control signal line that transmits an even column transfer control signal TGE for controlling the transfer transistors 261 of the pixels 26 in an even column.

A column selection signal line that transmits the selection control signal SEL is wired for each of the plurality of rows in which the shared pixels S are disposed. In the present embodiment, the column selection signal line is wired for every two rows. The column selection signal line is wired to pass through the region of the shared pixels S. The column selection signal line is connected to the selection transistors 265. The column selection signal line includes a column selection signal line that transmits an odd column selection control signal SELO for controlling the selection transistors 265 of the pixels 26 in an odd column, and a column selection signal line that transmits an even column selection control signal SELE for controlling the selection transistors 265 of the pixels 26 in an even column.

The transfer transistor 261, the reset transistor 263, and the selection transistor 265 are each either in an on state or an off state. Each of the transistors can be switched between the on state and the off state.

The state of the reset transistor 263 is controlled in response to the reset control signal RS. The state of the transfer transistor 261 is controlled in response to the transfer control signal TG. The state of the selection transistor 265 is controlled in response to the selection control signal SEL.

The image sensor 10 may be provided separately on two or more substrates. For example, the image sensor 10 is provided separately on an upper substrate and a lower substrate. The pixel array is disposed on the upper substrate. The column circuit unit 23 is disposed on the lower substrate. The pixel array is laminated on the upper substrate, and the column processing circuits 27 in the column circuit unit 23 of the lower substrate are disposed in parallel with the pixel columns of the pixel array of the upper substrate.

Figure 5:
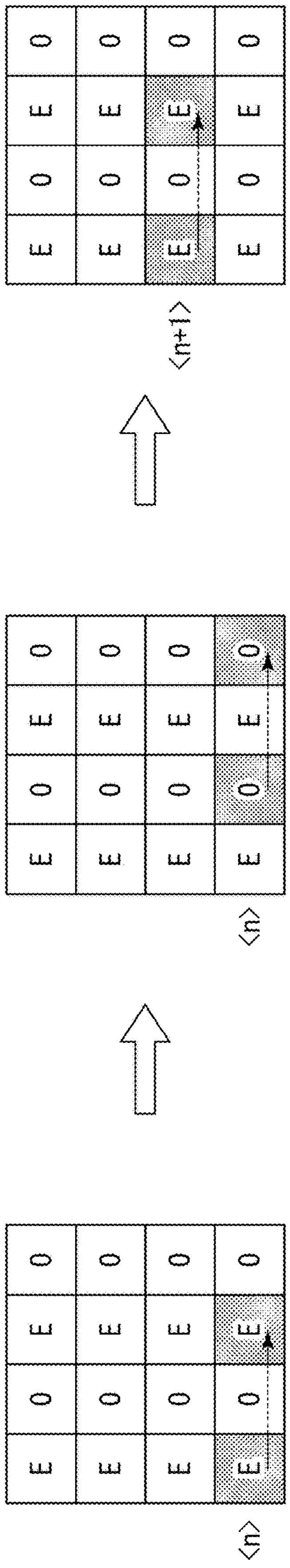
FIG. 5 is a diagram illustrating an operation of the image sensor.

Next, operations of the image sensor 10 will be described. FIG. 5 is a diagram illustrating the operations of the image sensor 10.

<Reading from Pixels in Odd Columns>

The vertical selection circuit 22 selects a row n in the pixel array. For the pixels 26 in the odd columns among the pixels 26 of the selected row n, the vertical selection circuit 22 controls the odd column selection control signal SELO to turn on the selection transistors 265. The vertical selection circuit 22 controls the reset control signal RS to set the FDs 262 to the reset level.

For the pixels 26 in the odd columns among the pixels 26 of the selected row n, the vertical selection circuit 22 controls the odd column transfer control signal TGO to turn on the transfer transistors 261. As a result, the first pixel signals and the second pixel signals are output from the pixels 26 to the vertical signal lines 30.

The column processing circuits 27 receive the first pixel signals and the second pixel signals via the vertical signal lines 30 and the shared vertical signal lines 31. The column processing circuits 27 selected on the basis of the selection pulses output the first pixel signals and the second pixel signals to the output unit 25.

<Reading from Pixels in Even Columns>

Next, for the pixels 26 in the even columns among the pixels 26 of the selected row n, the vertical selection circuit 22 controls the even column selection control signal SELE to turn on the selection transistors 265. That is, the vertical selection circuit 22, which controls the odd column selection control signal SELO and the even column selection control signal SELE in a time-division manner, controls the reset control signal RS to set the FDs 262 to the reset level.

For the pixels 26 in the even columns among the pixels 26 of the selected row n, the vertical selection circuit 22 controls the even column transfer control signal TGE to turn on the transfer transistors 261. As a result, the first pixel signals and the second pixel signals are output from the pixels 26 to the vertical signal lines 30.

The column processing circuits 27 receive the first pixel signals and the second pixel signals via the vertical signal lines 30 and the shared vertical signal lines 31. The column processing circuits 27 selected on the basis of the selection pulses output the first pixel signals and the second pixel signals to the output unit 25.

<Reading from Pixels in Next Row>

The vertical selection circuit 22 selects a row n+1 in the pixel array. The image sensor 10 performs the same processing on the row n+1 as on the row n in the pixel array. Then, the image sensor 10 performs the same processing on all remaining rows in the pixel array.

In the above reading method, the odd columns and the even columns are read out alternately, and thus crosstalk between adjacent pixels in the row direction R can be reduced.

<Other Aspects of Operations of Image Sensor 10>

Figure 6:
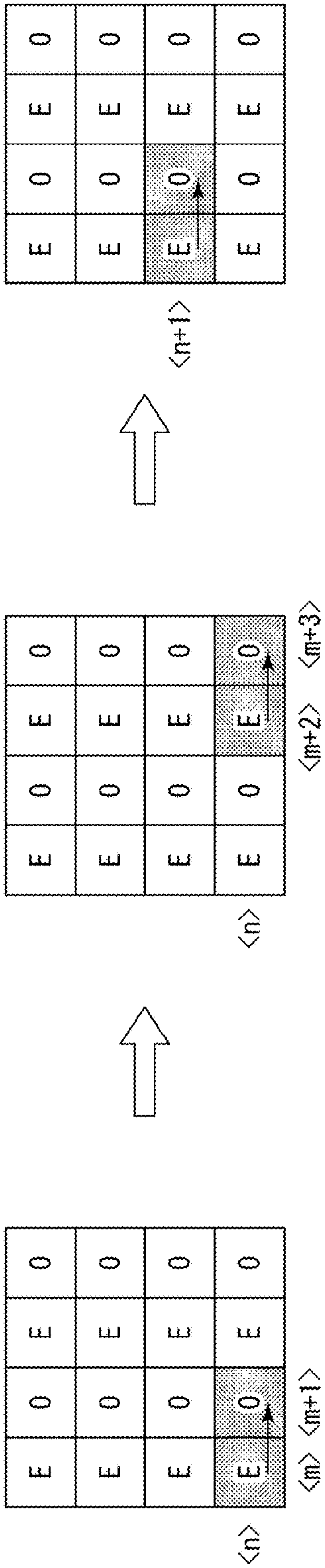
FIG. 6 is a diagram showing another aspect of the operation of the image sensor.

FIG. 6 is a diagram showing other aspects of the operations of the image sensor 10. The image sensor 10 may sequentially read signals from the pixels 26 in the row direction C for each row. In the example shown in FIG. 6, the image sensor 10 sequentially reads a column m, a column m+1, a column m+2, and a column m+3 in the row n. When reading of the row n is completed, the image sensor 10 starts to read the row n+1.

According to the image sensor (imaging element) 10 of the endoscope system 100 according to the present embodiment, since the vertical signal lines 30 adjacent to each other share the column processing circuit 27, the number of column processing circuits 27 to be mounted is reduced, and the degree of freedom in arranging the column processing circuits 27 is increased. As a result, the degree of freedom in the layout of the pixel array is increased, making it easier to implement a layout that miniaturizes the pixel array and maintains the symmetry of the pixels 26.

Although one embodiment of the present invention has been described above with reference to the drawings, the specific configuration is not limited to this embodiment, and design changes and the like that do not deviate from the gist of the present invention are also included. In addition, the constituent elements shown in the above embodiment and modified examples can be configured by appropriately combining them.

In the above embodiment, two vertical signal lines 30 adjacent in the row direction R are connected to one shared vertical signal line 31 outside the region of the pixel array, and the column processing circuit 27 is provided for each shared vertical signal line 31. However, the number of vertical signal lines 30 sharing one shared vertical signal line 31 may be three or more. In this case, there will be three or more transfer control signals TG and three or more selection control signals SEL.

The image sensor (imaging element) may output digital signals to the vertical signal lines 30.

The present invention can be applied to an image sensor (imaging device).

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An imaging device comprising a pixel array in which pixels including photoelectric conversion elements that perform photoelectric conversion are disposed in a matrix, wherein the photoelectric conversion elements of a plurality of the pixels adjacent in a column direction share a floating diffusion that accumulates photoelectrically converted charge, vertical signal lines that output signals based on the charge accumulated in the floating diffusion to the outside are wired to each column of the pixel array, a column selection signal line that transmits a selection control signal selecting one of a plurality of vertical signal lines adjacent in a row direction is wired within a region of the pixel array, and one column processing circuit that processes the signal is provided for the plurality of vertical signal lines selected by the selection control signal, wherein the plurality of vertical signal lines includes two vertical signal lines which are merged and directly connected to the column processing circuit, the pixels sharing the floating diffusion are two pixels in the column direction only.

2. The imaging device according to claim 1, wherein the pixels sharing the floating diffusion are two adjacent pixels in the column direction.

3. The imaging device according to claim 1, wherein the plurality of vertical signal lines selected by the selection control signal are connected to one shared vertical signal line outside the region of the pixel array, and the shared vertical signal line is connected to the column processing circuit.

4. The imaging device according to claim 1, wherein the column processing circuit is disposed in parallel with pixel columns of the pixel array outside the region of the pixel array.

5. The imaging device according to claim 1, further comprising:

an upper substrate on which the pixel array is disposed; and a lower substrate on which the column processing circuit is disposed, wherein the pixel array is laminated on the upper substrate, and the column processing circuit of the lower substrate is disposed in parallel with pixel columns of the pixel array of the upper substrate.

6. The imaging device according to claim 1, further comprising a transfer control signal line that selects one of shared pixels, which are the plurality of pixels sharing the floating diffusion, and transmits a transfer control signal for outputting the signal from the selected pixel to the outside, wherein the transfer control signal line is wired to pass through a region of the shared pixels.

7. The imaging device according to claim 6, wherein the column selection signal line is wired to pass through the region of the shared pixels.

8. The imaging device according to claim 6, further comprising a reset signal line that resets the charge accumulated in the floating diffusion, wherein the reset signal line is wired to pass through the region of the shared pixels.

9. The imaging device according to claim 8, wherein the reset signal line is wired to pass through a region of one pixel in the region of the shared pixels, and the column selection signal line is wired to pass through a region of another pixel in the region of the shared pixels.

10. The imaging device according to claim 8, wherein the shared pixels are two of the pixels adjacent in the column direction, the reset signal line is wired in a middle position between the shared pixels, and the column selection signal line is wired to pass through each region of the shared pixels.

11. The imaging device according to claim 1, wherein the column selection signal line includes:

a signal line that transmits an odd column selection control signal for selecting an odd column vertical signal line of two of the vertical signal lines adjacent in the row direction; and a signal line that transmits an even column selection control signal for selecting an even column vertical signal line of two of the vertical signal lines adjacent in the row direction, and the odd column selection control signal and the even column selection control signal are controlled in a time-division manner.

12. The imaging device according to claim 1, wherein the pixels sharing the floating diffusion are two pixels in the column direction, and the floating diffusion is disposed in a middle of the two pixels.

13. The imaging device according to claim 12, wherein numbers and positions of signal lines wired to pass through each of the two pixels are the same.

* * * * *